United States Patent [19]

Mitrani

[11] Patent Number: 4,589,878

[45] Date of Patent: May 20, 1986

[54] DISPOSABLE DIAPER

[75] Inventor: Sem Mitrani, Ris Orangis, France

[73] Assignee: Beghin-Say S.A., Thumeries, France

[21] Appl. No.: 593,920

[22] Filed: Mar. 27, 1984

[30] Foreign Application Priority Data

Mar. 29, 1983 [FR] France ............................. 83 05123

[51] Int. Cl.⁴ ............................................. A61F 13/16
[52] U.S. Cl. .................................. 604/392; 604/396; 604/400
[58] Field of Search .............. 604/392, 393, 394, 396, 604/400, 385, 386

[56] References Cited

U.S. PATENT DOCUMENTS

| 3,441,025 | 4/1969 | Ralph | 604/400 X |
| 3,575,172 | 4/1971 | Kiela | 604/385 R |
| 4,182,334 | 1/1980 | Johnson | 604/385 |
| 4,210,143 | 7/1980 | Dé Jonckheere | 604/392 X |
| 4,315,508 | 2/1982 | Bolick | 604/392 X |

FOREIGN PATENT DOCUMENTS 2033210  5/1980  United Kingdom ................ 604/385

Primary Examiner—Donald R. Valentine
Attorney, Agent, or Firm—A. W. Breiner

[57] ABSTRACT

A disposable diaper for incontinent adults comprising an absorbing pad covered by a liquid-impermeable external sheet (3) and a non-woven liquid-permeable inside sheet (4). This diaper is provided with four longitudinal folding lines, whereby it can be folded into several superposed levels (7a, 7b, 7c) when in the position of usage. Stretched elastic cords (13a) and (13b) are inserted between the sheets (3) and (4) near and parallel to the longitudinal edges. Prior to use two elastic belts (14a, 14b) are fixed on the same longitudinal edge (9a), one in the front zone (12) and the other in the rear zone (11) so as to clamp the cord (13a). The diaper has improved hermeticity and facilitates its emplacement by the user.

4 Claims, 5 Drawing Figures

DISPOSABLE DIAPER

The object of the present invention is a disposable diaper, in particular for incontinent adults, consisting of a flat absorbing pad of rectangular shape and covered on its external side by a liquid-impermeable sheet and on its inside, i.e., the side making contact with the skin of the user, by a non-woven, liquid-permeable sheet. The diaper is provided with a front and a rear zone.

Several diapers for incontinent adults have already been suggested. Among the diapers suggested there is, for instance, a diaper provided with two adhesive tapes located on each of the diaper's rear longitudinal edges. When in the position of use, each of the adhesive tapes is fastened to the corresponding front longitudinal edges. However, this fastening mode has certain drawbacks. Due to the position of the fasteners, the user must position himself with his back against the wall, or he must sit down, in order to put the diaper in place. Furthermore, this arrangement in practice requires that the diaper overlap on the sides.

The object of the diaper of the present invention is to alleviate the two above-cited drawbacks. Furthermore, the diaper of the disclosed invention provides additional advantages in that it has improved hermeticity, and a single size diaper fits anyone.

The invention is characterized in that near each of the longitudinal edges of the diaper pad and along its entire length strings are provided, and in that prior to use an elastic belt consisting of an elastic band provided with fasteners is fastened near its rear zone on one of the longitudinal edges so that the fastener clamps the string. A second elastic belt similar to the first is fastened on the same longitudinal edge near the front zone so that the fastener of the second belt also clamps the string. As a rule, the absorbing diaper pad is made of cellulose foam into which may be incorporated hydrocolloidal materials which absorb several times their weight in liquids. The liquid-impermeable sheet generally is a polyethylene.

The diaper may be quasi-rectangular; accordingly, there is no need to provide sideways extensions in the front and rear zones. The diaper may be plane in a single composite layer, or on the contrary it may also be symmetrically folded back about its longitudinal axis to obtain several superposed thicknesses as described, for instance, in French Pat. No. 2,181,792.

The diaper rear zone is that zone which, when the diaper is in its position of usage, is located near the waist and at the back of the user. The front zone is the zone opposite of the rear zone.

The string is obtained, for instance, by means of a cord inserted between a sheet and the pad; or else when the sheets extend laterally beyond the pad edges this cord can be sandwiched between the two sheets. Preferably the cord is elastic and is fixed pre-stressed on the entire length of the longitudinal edge, whereby the elasticity of the elastic bands is thus combined with the elasticity of the cord, providing better hermeticity.

The invention will be better understood in relation to the detailed description below of a preferred illustrative embodiment of the invention and the attached drawings.

Figure 1:
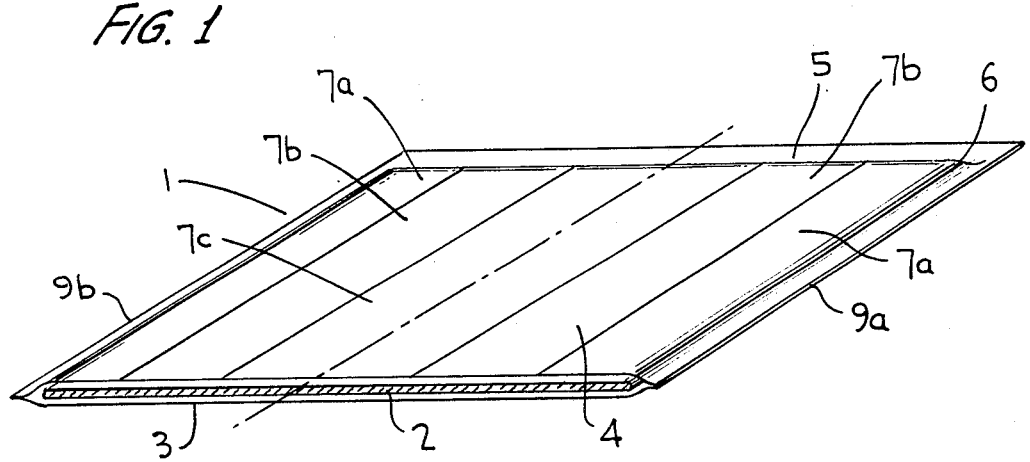
FIG. 1 is a perspective view of a diaper laid flat, a section thereof showing the various constitutive means.
Figure 2:
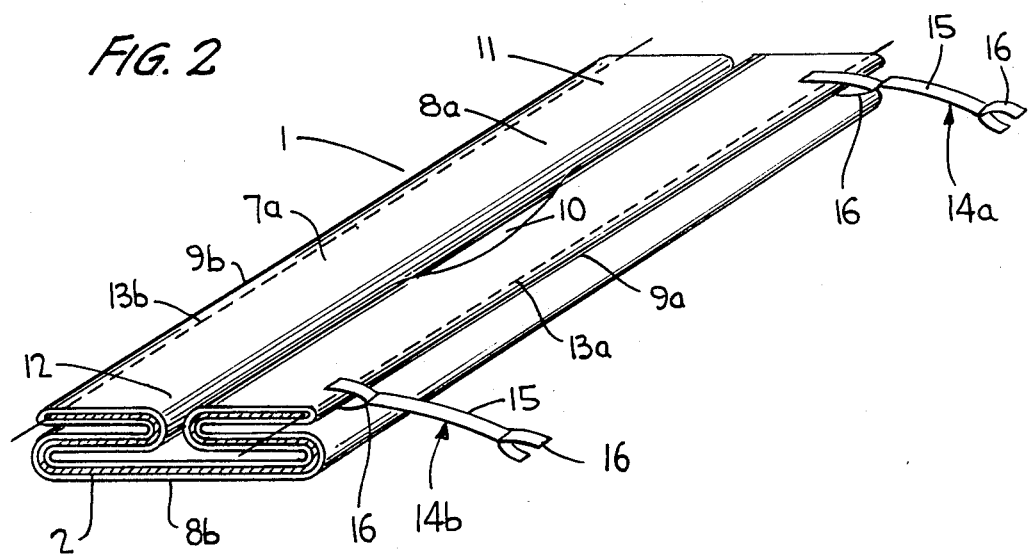
FIG. 2 is a perspective view of a diaper ready for use, with the elastic belt having end fasteners attached.
Figure 3:
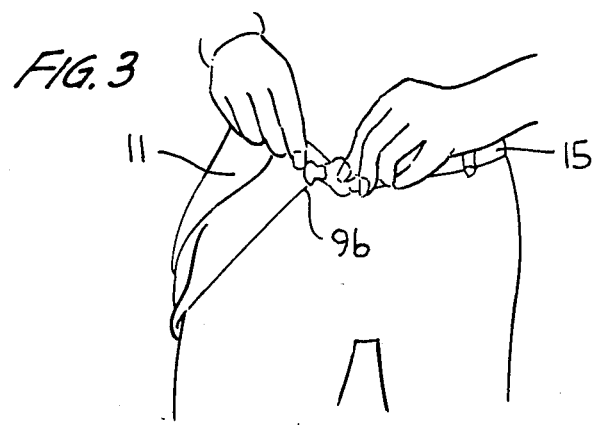
Figure 4:
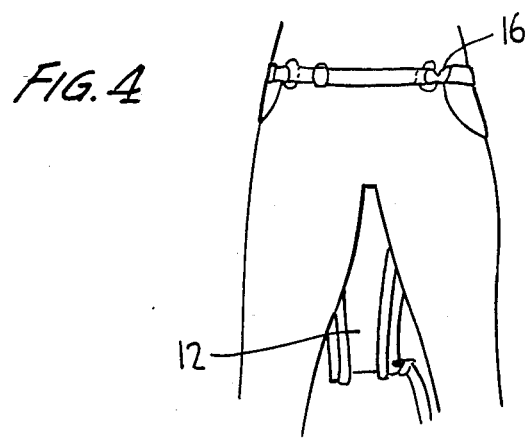
Figure 5:
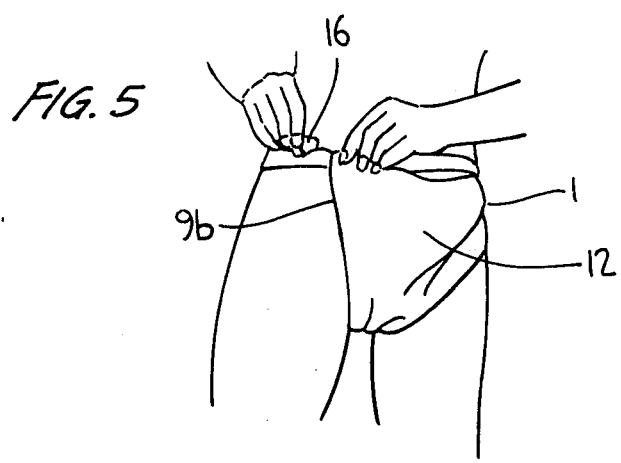

FIGS. 3, 4, and 5 show how the user puts the diaper in place.

A rectangular diaper 1 consists of an absorbing pad 2 made of cellulose foam and covered on one side by an impermeable polyethylene sheet 3, and on the other side by a nonwoven permeable sheet 4. The area of the absorbing pad is less than that of the sheets 3 and 4, whereby the pouch can be closed, and lateral and longitudinal strips 6 and 5, respectively, can be formed.

This diaper is provided with four longitudinal folding lines arranged pairwise symmetrically and parallel to its longitudinal axis. These folding lines define four strips:

two external strips 7a, two strips 7b which are adjacent to the external strips and located on either side of a median strip 7c of which the area is substantially equal to twice the area of each of the strips 7a and 7b. In the position of usage, the adjacent strips 7b are folded in such a manner that they cover approximately a half-area of the non-woven material 4 of the median strip 7c, while the external strps 7a are folded so that the polyethylene side of these strips covers the polyethylene side of strips 7b which are adjacent to the external strips. In this manner the non-woven surfaces of the external strips 7a constitute, possibly together with part of the median strip 7c, the diaper inside 8a which will come into contact with the skin of the user; and the polyethylene surface of the median strip 7c constitutes the diaper outside 8b. The outer edges of the external strips 7a form the diaper longitudinal edges 9a and 9b. The non-woven areas of the adjacent strips 7b can be solidly joined to the median strip 7c at least near the central zone 10.

Elastic cords 13a and 13b are inserted in the stretched state between the sheets 3 and 4 near the sideways bands 6, and near and parallel to the longitudinal edges 9a and 9b. These elastic cords 13a and 13b serve two functions:

they facilitate keeping in place the fastening means described below, and they provide improved hermeticity by "extending" the elasticity of the elastic bands.

The elastic belts 14a and 14b consist of an elastic band 15 terminating at each end in a jaw-shaped fastener 16. Advantageously, the length of these belts will be adjustable. One of the fasteners 16 of a first elastic belt 14a is fixed transversely with respect to the longitudinal axis near the longitudinal edge 9a and in the rear zone 11 so as to clamp the elastic cord 13a and be located near the user's waist. One of the fasteners 16 of a second elastic belt 14b is fixed transversely near the same longitudinal edge 9a in the fore zone 12 so as to clamp the elastic cord 13a and be located near the waist.

As shown in FIGS. 3, 4, and 5, with the inside 8a of the rear zone 11 placed against the hip of the user with one hand, and with the longitudinal edge 9a holding the elastic belts 14a, 14b being toward the back of the wearer, the user pulls the free fastener 16 of the elastic belt 14a located near the rear zone 11 from behind his back to the front of him and fastens it to the other longitudinal edge 9b of the rear zone 11, then he moves the diaper rear zone 11 towards the back. The front zone 12 of the diaper is next raised between the legs and the free fastener 16 of the other elastic belt 14b is pulled around so as to pass behind the user's back, being placed forward, so as to fasten it to the other longitudinal edge 9b of the front zone 12.

As will be apparent to one skilled in the art, various modifications can be made within the scope of the aforesaid description. Such modifications being within the ability of one skilled in the art form a part of the present invention and are embraced by the appended claims.

It is claimed:

1. A disposable diaper, in particular for incontinent adults, comprising an absorbing, flat pad of rectangular shape and covered on its outside by an impermeable sheet and on its inside which will make contact with the user's skin by a non-woven permeable sheet, said diaper being provided along a longitudinal axis with a rear zone and a front zone, characterized in that strings are provided near each of the longitudinal edges and along their entire length, in that prior to use a first elastic belt provided with a fastener at each end is fastened in the rear zone a first longitudinal edge so as to fasten the string of said edge, a second similar elastic belt provided with a fastener at each end is fastened to said first longitudinal edge in the front zone so that the fastener of the second belt also fastens the string to said edge whereby, in use, said first and second belt are fastened to the second longitudinal edge, respectively, in the rear zone and in the front zone so as to fasten the string of said second longitudinal edge.

2. Disposable diaper according to claim 1 wherein said strings are cords clamped between the permeable sheet and the impermeable sheet.

3. Disposable diaper according to claim 2 wherein said strings are elastic and when in the stretched state span the entire length of the longitudinal edge.

4. Disposable diaper according to claim 1 wherein said elastic belts are fixed in place transversely to the diaper's longitudinal axis.

* * * * *